United States Patent [19]
Chang

[11] Patent Number: 5,912,367
[45] Date of Patent: Jun. 15, 1999

[54] HIGH EFFICIENCY EPOXIDATION PROCESS

[75] Inventor: Te Chang, West Chester, Pa.

[73] Assignee: Arco Chemical Technology, L.P., Greenville, Del.

[21] Appl. No.: 08/886,628

[22] Filed: Jul. 1, 1997

[51] Int. Cl.[6] .................... C07D 301/12; C07D 301/19
[52] U.S. Cl. ............................. 549/529; 549/531
[58] Field of Search ...................... 549/529, 531

[56] References Cited

U.S. PATENT DOCUMENTS

| | | | |
|---|---|---|---|
| 4,367,342 | 1/1983 | Wulff et al. | 549/529 |
| 4,833,260 | 5/1989 | Neri et al. | 549/531 |

Primary Examiner—Ba K. Trinh
Attorney, Agent, or Firm—Stephen D. Harper

[57] ABSTRACT

Propylene is converted to propylene oxide in a highly efficient liquid phase process wherein temperature and pressure are both increased over the course of the epoxidation, which is preferably conducted in a continuous mode of operation. The catalyst used is a heterogeneous catalyst such as titanium silicalite or titania-on-silica. The oxidizing agent is an active oxygen species such as hydrogen peroxide or an organic hydroperoxide. When the desired yield of propylene oxide can no longer be maintained, the catalyst is replaced or regenerated. Regeneration by washing the catalyst with a hot solvent containing a source of ammonium or alkali metal cations is highly

16 Claims, No Drawings

HIGH EFFICIENCY EPOXIDATION PROCESS

FIELD OF THE INVENTION

This invention relates to propylene epoxidation processes capable of maintaining high yields of propylene oxide over an extended period of time. Propylene and an active oxygen species are reacted in a liquid phase in the presence of a heterogeneous epoxidation catalyst under conditions of increasing temperature and pressure to compensate for the gradual deactivation of the catalyst. Periodic regeneration and/or replacement of the catalyst once it is no longer capable of providing the desired levels of active oxygen species conversion and epoxide selectivity is practiced.

BACKGROUND OF THE INVENTION

Over the last several decades, different types of insoluble substances have been found to be highly active and selective catalysts for transforming olefins such as propylene to epoxides such as propylene oxide using active oxygen species. One class of such catalysts includes the titanium silicalites such as TS-1 and other zeolites having titanium atoms in their framework structures, which work well where the oxidant is hydrogen peroxide and the olefin is relatively small. See, for example, U.S. Pat. No. 4,833,260. When the active oxygen species is an organic hydroperoxide such as ethyl benzene hydroperoxide, the use of porous amorphous catalysts such as those commonly referred to as "titania-on-silica" is preferred. Olefin epoxidation using such catalysts is described, for example, in U.S. Pat. No. 4,367,342.

Although heterogeneous epoxidation catalysts typically exhibit high activity and selectivity when freshly prepared, gradual deactivation takes place simultaneously with epoxidation. This problem is particularly acute in a large scale continuous commercial operation where, for economic reasons, an epoxidation process must be capable of being operated over an extended period of time while maintaining high yields of epoxide. Although regeneration methods for such catalysts are known, it would be highly advantageous to develop procedures whereby the interval between regenerations is extended for as long as possible. Regeneration requires that epoxidation be interrupted for some period of time sufficient to effect catalyst reactivation, thereby reducing the effective annual capacity of a commercial plant. The deactivated catalyst could alternatively be replaced with fresh catalyst, but the same practical disadvantages will result as with regeneration. Additionally, catalysts of this type tend to be relatively costly and it would be desirable to minimize the quantity of fresh catalyst which is needed to supply the plant.

SUMMARY OF THE INVENTION

A improved method for operating a propylene oxide process has been discovered comprising:

(a) contacting propylene with an active oxygen species in a liquid phase utilizing a heterogeneous catalyst at a temperature and pressure effective to obtain at least a desired minimum yield of propylene oxide; and (b) increasing both the temperature and pressure in a manner effective to maintain a substantially constant concentration of propylene in the liquid phase and to continue to obtain at least the desired minimum yield of propylene oxide.

DETAILED DESCRIPTION OF THE INVENTION

In the process of this invention, propylene is reacted with an active oxygen species to form the corresponding epoxide (propylene oxide). The active oxygen species may be any compound capable of functioning as a source of the oxygen atom to be transferred to the olefin during epoxidation. Particularly preferred active oxygen species include hydrogen peroxide, organic hydroperoxides, and precursors thereof. For example, hydrogen peroxide or an organic hydroperoxide may be supplied as such to the epoxidation zone or may be generated in situ during epoxidation.

It is generally preferred to operate at a molar ratio of active oxygen species:propylene in the range of from 1:1 to 1:30 (more preferably, from 1:5 to 1:20). As will be explained in more detail later, however, it is critical to maintain a substantially constant concentration of propylene in the liquid phase.

The hydrogen peroxide which may be utilized as the oxidizing agent may be derived from any suitable source. For example, the hydrogen peroxide may be obtained by contacting a secondary alcohol such as alphamethyl benzyl alcohol, isopropyl alcohol, 2-butanol, or cyclohexanol with molecular oxygen under conditions effective to form an oxidant mixture comprised of secondary alcohol and hydrogen peroxide (and/or hydrogen peroxide precursors). Typically, such an oxidant mixture will also contain a ketone such as acetophenone, acetone, or cyclohexanone corresponding to the secondary alcohol (i.e., having the same carbon skeleton), minor amounts of water, and varying amounts of other active oxygen species such as organic hydroperoxides. One or more of the components of the oxidant mixture such as ketone may be removed in whole or in part prior to epoxidation. Molecular oxygen oxidation of anthrahydroquinone, alkyl-substituted anthrahydroquinones, or water-soluble anthrahydroquinone species may also be employed to generate the hydrogen peroxide.

The organic hydroperoxides usable as the active oxygen species in the epoxidation process of this invention may be any organic compound having at least one hydroperoxy functional group (—OOH). Secondary and tertiary hydroperoxides are preferred, however, owing to the higher instability and greater safety hazards associated with primary hydroperoxides. The organic hydroperoxide preferably has the general structure:

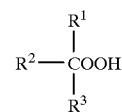

wherein $R^1$, $R^2$ and R3 are the same or different and are selected from the group consisting of hydrogen, $C_1$–$C_{10}$ alkyl (e.g., methyl, ethyl, t-butyl) and $C_6$–$C_{12}$ aryl (e.g., phenyl, alkyl substituted phenyl), subject to the proviso that not more than one of $R^1$, $R^2$, or $R^3$ is hydrogen. Exemplary organic hydroperoxides include t-butyl hydroperoxide, t-amyl hydroperoxide, cumene hydroperoxide, ethyl benzene hydroperoxide, cyclohexyl hydroperoxide, methyl cyclohexyl hydroperoxide, tetralin hydroperoxide, isobutyl benzene hydroperoxide, ethyl naphthalene hydroperoxide, and the like. Mixtures of organic hydroperoxides may also be employed.

The concentration of the active oxygen species in the liquid phase is not regarded as critical. Generally speaking, concentrations of from about 1 to 30 weight percent are suitable. The optimum concentration will depend upon the active oxygen species and heterogeneous catalyst selected for use, the liquid phase propylene concentration, and the active oxygen species:propylene molar ratio, among other factors. The liquid phase active oxygen species concentration may, of course, vary over the length of the reactor due to the reaction of the active oxygen species as it passes through the reactor or the introduction of the additional quantities of active oxygen species at different points within the reactor (staged addition).

A distinguishing feature of the present invention is that the concentration of propylene in the liquid phase at a given point within the reactor is maintained at a substantially constant level during operation. The temperature at said point is increased over the course of the epoxidation in order to keep the epoxide yield at or above the desired minimum level. The propylene oxide yield is a function of both conversion and selectivity. "Conversion" as used herein refers to the quantity of active oxygen species which is reacted in the course of passing through the reactor compared to the quantity of active oxygen species introduced to the reactor. "Selectivity" as used herein refers to the number of equivalents of propylene oxide produced per equivalent of active oxygen species reacted. The percent "yield" of propylene oxide thus may be calculated as conversion (in %) times selectivity (in %) divided by 100. For example, where the hydrogen peroxide conversion is 98% and the propylene oxide selectivity is 85%, the yield of propylene oxide is 83.3%. One of the objects of this invention is to operate the epoxidation such that the yield of propylene oxide is at or above a certain minimum value deemed acceptable from a commercial and economic point of view. Where the active oxygen species is hydrogen peroxide and the catalyst is a titanium-containing zeolite, for example, it is particularly desirable for the propylene oxide yield to be 80% or higher. Where the active oxygen species is an organic hydroperoxide and the catalyst is titania-on-silica, the process is desirably operated to achieve a propylene oxide yield of at least 85%.

As the heterogeneous catalyst is used to catalyze epoxidation in a continuous process, it will exhibit a gradual loss in activity as reflected in a decrease in active oxygen species conversion under a given set of conditions. Some decline in selectivity may also be observed over time. To compensate for catalyst deactivation, the temperature at which the propylene and the active oxygen species are contacted in the presence of the catalyst is increased. The temperature increases may be performed in either a continuous or incremental manner. The rate at which temperature is increased may be either linear or exponential, depending upon the deactivation characteristics of the particular epoxidation system being utilized. Since the rate at which the active oxygen species reacts is temperature dependent, this will lead to an increase in conversion so the desired minimum propylene oxide yield can continue to be met or exceeded. However, it has been found that increasing the epoxidation temperature results in a lower proportion of the propylene, a highly volatile olefin, being dissolved in the liquid phase within the reactor, particularly where the reactor is a vaporizing reactor. This, in turn, has a detrimental effect on propylene selectivity since selectivity is dependent upon the propylene:active oxygen species molar ratio within the liquid phase. By increasing the pressure within the reactor simultaneously with the temperature, however, the propylene concentration in the liquid phase may be maintained substantially constant so that the selectivity is improved and the propylene oxide yield still attained.

The temperature, pressure, and liquid phase propylene concentration ranges selected for use with the present invention will vary somewhat depending upon the catalyst and active oxygen species employed. For example, the desirable temperature range is generally somewhat lower using a titanium silicalite catalyst and hydrogen peroxide (e.g., 40° C. to 80° C.) than when a titania-on-silica catalyst and organic hydroperoxide are utilized (e.g., 80° C. to 130° C.) although overlap of these ranges is possible. The initial temperature (or initial temperatures, where temperature is varied over the length of a reactor) will normally be the lowest temperature(s) at which the desired minimum yield of propylene oxide can be obtained. The maximum temperature(s) will be determined by the temperature(s) at which the desired minimum propylene oxide yield can no longer be sustained due to increasing competition from non-selective decomposition of the active oxygen species and sequential reactions of the desired epoxide product. Typically, the difference between the initial temperature and the final temperature (i.e., the temperature at which regeneration is required) will be at least 5° C. but no greater than 40° C. and in many cases (especially where the active oxygen species is hydrogen peroxide and the catalyst is a titanium-containing zeolite) no greater than 25° C.

As discussed previously, the concentration of propylene in the liquid phase at a given point within the reactor will be kept substantially constant over the course of the epoxidation cycle and will typically be in the range of from about 20 to 60 weight percent. Lower concentrations within this range (e.g., 20 to 40 weight percent) are generally preferred where the active oxygen species is hydrogen peroxide and the catalyst is a titanium-containing zeolite. "Substantially constant" in this context means that the propylene concentration varies no more than about 5 weight percent (plus or minus) on an absolute basis from a given value, with variations of no more than about 1 weight percent (plus or minus) being preferred. The liquid phase propylene concentration may, however, be different at different points within the reactor at any given moment, as may be desirable to effect volatilization of the propylene and/or propylene oxide and remove all or a portion of the heat of reaction generated while passing the liquid phase through one of the reaction zones (e.g., individual fixed beds) within the reactor.

The pressure at which the epoxidation process is operated is selected based on the temperature and propylene concentration which are employed. As temperature is increased, for example, the pressure must correspondingly be increased to maintain a liquid phase propylene concentration which is substantially constant over time at a given point within the reactor. Pressures within the range of from about 150 to 1000 psia are usually sufficient for such purpose.

If desired, a solvent may additionally be present during the epoxidation process of this invention in order to dissolve the reactants other than the heterogeneous catalyst, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature.

Organic compounds having boiling points at atmospheric pressure of from about 25° C. to 300° C. are generally preferred for use. Excess propylene may serve as a solvent or diluent. Illustrative examples of other suitable solvents include, but are not limited to, ketones (e.g., acetone, methyl ethyl ketone, acetophenone), ethers (e.g., tetrahydrofuran, butyl ether), nitriles (e.g., acetonitrile), aliphatic and aromatic hydrocarbons (e.g., ethyl benzene, cumene), halogenated hydrocarbons, and alcohols (e.g., methanol, ethanol, isopropyl alcohol, t-butyl alcohol, alpha-methyl benzyl alcohol, cyclohexanol). Where the catalyst is a titanium silicalite and the active oxygen species is hydrogen peroxide, the use of alcohols as solvents is preferred (methanol and isopropanol being particularly preferred). Such reaction systems can also tolerate substantial quantities of water without detrimental effect. If an organic hydroperoxide such as ethylbenzene hydroperoxide is utilized together with a titania-on-silica catalyst, then it is preferred that the hydrocarbon corresponding to the hydroperoxide (e.g., ethyl benzene) be used as the solvent with water being substantially excluded.

The catalyst employed in the present process may be any substance which is insoluble in the liquid phase of the epoxidation reaction mixture and capable of catalyzing the transformation of propylene to propylene oxide. Such catalysts are well-known in the art and may be of a crystalline (e.g., zeolitic) or amorphous character. Titanium-containing catalysts are particularly preferred for purposes of this invention.

Illustrative catalysts include titanium-containing molecular sieves comprising the class of zeolitic substances wherein titanium atoms are substituted for a portion of the silicon atoms in the lattice framework of a molecular sieve.

Particularly preferred titanium-containing molecular sieves include the molecular sieves commonly referred to as "TS-1" (having an MFI topology analogous to that of the ZSM-5 aluminosilicate zeolites; see U.S. Pat. No. 4,410,501), "TS-2" (having an MEL topology analogous to that of the ZSM-11 aluminosilicate zeolites), "TS-3" (as described in Belgian Pat. No. 1,001,038), "TS-48" (having a ZSM-48 structure, and "TS-12" (having an MTW-type structure). Also suitable for use are the titanium-containing molecular sieves having framework structures isomorphous to zeolite beta as well as those materials designated "CIT-1", "SSZ-33", "ETS-4", "ETS-10", and "Ti-MCM-41". The titanium-containing molecular sieves preferably do not contain elements other than oxygen, titanium and silicon in the lattice framework, although minor amounts of boron, iron, aluminum, and the like may be present. Titanium-containing molecular sieves usable in the present process are sometimes variously referred to by workers in the field as "titanium silicalites", "titanosilicates", "titanium silicates", "silicon titanates" and the like.

Titanium-containing molecular sieves suitable for use in the process of this invention will generally have a composition corresponding to the following empirical formula $x\text{TiO}_2:(1-x)\text{SiO}_2$, where $x$ is between 0.0001 and 0.500. More preferably, the value of $x$ is from 0.01 to 0.125. The molar ratio of Si:Ti in the lattice framework of the titanium-containing molecular sieve is advantageously from 9.5:1 to 99:1 (most preferably, from 9.5:1 to 60:1). Large pore (mesoporous) as well as small pore (microporous) molecular sieves are suitable for use.

Other suitable catalyst compositions are substances comprising an inorganic oxygen compound of silicon in chemical combination with an inorganic oxygen compound of titanium (e.g., an oxide or hydroxide of titanium). The inorganic oxygen compound of titanium is preferably combined with the oxygen compound of silicon in a high positive oxidation state, e.g., tetravalent titanium. The proportion of the inorganic oxygen compound of titanium contained in the catalyst composition can be varied, but generally the catalyst composition contains, based on total catalyst composition, at least 0.1% by weight of titanium with amounts from about 0.2% by weight to about 50% by weight being preferred and amounts from about 0.2% to about 10% by weight being most preferred.

Catalysts of this type are well-known in the art and are described, for example, in U.S. Pat. Nos. 4,367,342, 4,021,454, 3,829,392 and 3,923,843, European Patent Publication Nos. 0129814, 0345856, 0492697 and 0734764, Japanese Kokai No. 77-07,908 (Chem. Abstracts 87:135000s), PCT Application No. WO 94/23834, German Patent Document No. 3,205,648, and Castillo et al., *J. Catalysis* 161, pp. 524–529 (1996).

The inorganic oxygen compound of silicon is an inorganic siliceous solid containing a major proportion of silica. Amorphous (i.e., non-crystalline) silicon compounds are particularly preferred for use. In general, suitable inorganic siliceous solids are further characterized by having a relatively large surface area in relation to their mass. The term used herein and one normally used in the art to express the relationship of surface area to mass is "specific surface area". Numerically, specific surface area will be expressed as square meters per gram ($m^2/g$). Generally, the inorganic siliceous solid has a specific surface area of at least 1 $m^2/g$ and preferably the average specific surface area is from 25 $m^2/g$ to 800 $^2/g$.

Suitable inorganic siliceous solids include synthetic porous silicas consisting of particles of amorphous silica flocculated or linked together so that they form relatively dense, close-packed masses. Representatives of such materials are silica gel and precipitated silica. These silica products are porous, in that they have numerous pores, voids, or interstices throughout their structures.

One type of heterogeneous catalyst particularly suitable for use in the present invention is titania-on-silica (also sometimes referred to as "TiO$_2$/SiO$_2$"), which comprises titanium (titanium dioxide) supported on silica (silicon dioxide). The titania-on-silica may be in either silylated or nonsilylated form.

Preferably, the catalyst is deployed in the form of a fixed bed (or a plurality of separate fixed beds) with the liquid phase comprising the reactants (propylene and active oxygen species) being passed through the packed bed(s) of solid catalyst. Each catalyst bed may be considered a reaction zone within which the heterogeneous titanium-containing catalyst is contacted with propylene and the active oxygen species in the liquid phase to form propylene oxide. Epoxidation is conducted preferably on a continuous basis with one or more feed streams comprising the reactants being introduced to the reactor while simultaneously withdrawing one or more product streams comprising propylene oxide from the reactor. Vaporizing reactors, wherein the heat of reaction is controlled by permitting volatilization of propylene and/or propylene oxide from the reaction mixture, are especially preferred for use. Reactors of this type offer significant cost advantages over other types of reactors when used for highly exothermic epoxidations. Part of the heat generated by the exothermic epoxidation may be removed by other means such as indirect heat exchange (e.g., cooling of portions of the liquid phase withdrawn from the reactor followed by return of the cooled liquid phase to the reactor).

The catalytic converter systems described in U.S. Pat. No. 5,466,836, U.S. Ser. No. 08/740,461 (filed Oct. 29, 1996), U.S. Ser. No. 08/791,796 (filed Jan. 29, 1997) and EP 323663 may also be utilized if so desired. Each of the foregoing documents is incorporated hereby by reference in its entirety.

Depending upon the reactor configuration and heat removal means selected, the temperature of the liquid phase as it passes through each reaction zone may either be kept substantially constant (i.e., the liquid phase temperature is not significantly different from point to point along the length of the reaction zone at a given time) by removing all or nearly all of the heat of reaction or be permitted to increase to a moderate degree (i.e., the liquid phase temperature is progressively higher at downstream points in the reaction zone than the liquid phase temperature at the point at which the liquid phase first enters the reaction zone) by removing none or only a portion of the heat of reaction. For example, the liquid phase temperature may rise 0° C. to 40° C. across an individual catalyst bed. The process of this invention may be readily adapted to either mode of operation by increasing over a period of time the liquid phase temperature and pressure at any given point or points of the fixed catalyst bed. For example, upon start-up of epoxidation the liquid phase temperature may be adjusted such that a temperature of 50° C. is maintained at Point A of a fixed catalyst bed where the liquid phase is first contacted with the catalyst bed and a temperature of 60° C. is maintained at Point B of the fixed catalyst bed where the liquid phase exits from the catalyst bed. This rise in temperature along the catalyst bed is attributable to the exothermic epoxidation which takes place, with the heat of reaction being permitted to increase the liquid phase temperature rather than being completely removed by cooling means. As the catalyst begins to deactivate over a period of time (typically, days or weeks), the liquid phase temperatures at Point A and Point B may be incrementally increased to 55° C. and 65° C., respectively, to maintain the propylene oxide yield at or above the desired value. The pressure at Point A and the pressure at Point B (which may or may not be different) are similarly adjusted upwards over this period of time such that the liquid phase propylene concentrations at Point A and Point B (which may or may not be different from each other) remain substantially unchanged.

When the catalyst has deactivated to an extent that further increases in temperature fail to maintain the epoxide yield above the minimum value due to competition from non-selective reactions of the active oxygen species, propylene or propylene oxide, the epoxidation is interrupted and regeneration or replacement of the catalyst carried out. An important advantage of the present invention is that it permits more complete utilization of a propylene oxide plant by minimizing the number of times per year an individual reactor needs to be shut down or taken off-line and by maximizing the quantity of propylene oxide which is produced between each catalyst regeneration or replacement. Increasing the epoxidation cycle time (i.e., lengthening the period of time between catalyst regeneration or replacement) improves significantly the overall efficiency of a propylene oxide process.

Regeneration of the catalyst may be conducted in accordance with any of the procedures known in the art such as calcination, solvent washing, and/or treatment with various reagents. In the embodiment where the catalyst is deployed in fixed bed form, it is highly desirable to practice a regeneration technique where the catalyst is reactivated in place (i.e., without removal from the epoxidation reactor). This will, generally speaking, further enhance the overall efficiency of the process by minimizing the amount of time the process is off-line since discharging the catalyst from the reactor and then recharging it is typically quite time-consuming.

Suitable regeneration techniques are well-known in the art and are described, for example, in Japanese Laid-Open Patent Application No. 3-114536, G. Perego et al. Proc. 7th Intern. Zeolite Confer. 1986, Tokyo, p. 827, EP 0743094, and U.S. Pat. No. 5,620,935. Where the catalyst is a titanium-containing molecular sieve such as a titanium silicalite, it is particularly advantageous to employ a regeneration procedure wherein the catalyst is washed at an elevated temperature with a solvent containing a source of ammonium or alkali metal cations. Suitable temperatures include the range of from 125° C. to 250° C. The solvent is preferably a relatively polar solvent such as a $C_1$–$C_6$ aliphatic alcohol (e.g., methanol, ethanol, n-propanol, isopropanol, t-butanol), water or a mixture thereof which is capable of dissolving the desired concentration of the cation source. The source of ammonium or alkali metal cations may be an acidic, neutral or basic salt such as, for example, an ammonium and alkali metal salt of phosphoric acid, sulfuric acid, carboxylic acid, carbonic acid, nitric acid, hydrohalide acid, and the like. Ammonium and alkali metal hydroxides are also suitable for use. Illustrative compounds of this type include, but are not limited to, ammonium hydroxide, sodium chloride, potassium nitrate, sodium sulfate, potassium carbonate, sodium bicarbonate, sodium acetate, sodium phosphates, and sodium hydroxide. The concentration of the salt in the solvent may vary considerably depending upon the identity of the salt and other factors, but typically is in the range of from about 5 to 1000 parts per million (more preferably, 10 to 500 parts per million). The solvent is contacted with the spent catalyst, preferably by passing the solvent through a fixed bed of the catalyst, for a period of time effective to restore catalyst performance to the desired level, typically, from about 0.5 to 24 hours. The regenerated catalyst is thereafter reused for epoxidation as previously described herein. The use of the source of an ammonium or alkali metal cation source unexpectedly provides catalysts which more quickly reach high epoxide yields upon recommencement of epoxidation. That is, solvent washing alone will furnish catalysts capable of operating at high activity and selectivity, but only after a longer period of operation than is the case when regeneration is performed in the presence of ammonium or alkali metal cations. Following regeneration or replacement of the catalyst, epoxidation may be reinitiated in accordance with the foregoing description wherein temperature and pressure are both increased over time in order to meet or exceed the desired yield of propylene oxide.

EXAMPLES

Example 1 (Comparative)

Propylene epoxidation was conducted in a three stage reactor (spinning basket CSTR followed by two fixed bed reactors) using a synthetic concentrated isopropanol oxidate containing 16.5 weight % of hydrogen peroxide in a 3.2/1 isopropanol/water mixture (spiked with low levels of organic acid impurities) and TS-1 titanium silicalite (10 g per stage) as catalyst. The reactor pressure was held substantially constant at about 300 psia while the temperature was increased from 65.6° C. to 71.1° C. over 85 hours in order to maintain the hydrogen peroxide conversion at 98.5%. The weight hourly space velocity was 0.54, based on grams of hydrogen peroxide per gram TS-1 titanium silicalite per hour. A diluent, which simulates a solvent recycle, was also fed to the reactor to dilute the hydrogen peroxide concentration to 5.4 weight %. The diluent feed was a mixture of isopropanol and water at a ratio of 6.3:1 containing 100 ppm ammonium hydroxide. As shown in the following table, selectivity to propylene oxide based on hydrogen peroxide decreased significantly as the temperature was increased.

| Temp., °C | Pressure, psia | PO Selectivity, % | Propylene in Liquid Phase, wt. % |
|---|---|---|---|
| 65.6 | 301 | 86 | 30.1 |
| 68.3 | 298 | 84 | 26.3 |
| 71.1 | 298 | 83 | 24.1 |

Example 2

This example demonstrates the advantages of operating a propylene epoxidation in accordance with the present invention. The procedure of Example 1 was repeated, except that the pressure was increased during the course of epoxidation to maintain a substantially constant concentration of propylene in the liquid phase over an 85 hour period. The data in the following table confirm that higher selectivity to propylene oxide was achieved compared to Example 1, where pressure was not increased.

| Temp., °C | Pressure, psia | PO Selectivity, % | Propylene in Liquid Phase, wt. % |
|---|---|---|---|
| 65.6 | 301 | 86 | 30.1 |
| 68.3 | 318 | 85.5 | 29.9 |
| 71.1 | 336 | 85 | 29.8 |

Example 3

Titanium silicalite catalyst which had been used for an extended period of time in a propylene epoxidation process similar to that described in Example 2 was regenerated by washing with the mixture of isopropanol and water described in Example 1 as a feed diluent. A total of 210 g of the mixture was fed continuously through 30 g TS-1 over 3 hours at 182° C. The beneficial effect of incorporating 100 ppm ammonium hydroxide in the solvent mixture was demonstrated as shown in the following table.

| Type of Catalyst | Fresh | Regenerated | Regenerated |
|---|---|---|---|
| NH$_4$OH in Solvent? | — | No | Yes |
| Epoxide Selectivity after 8 hours (%, based on H$_2$O$_2$) | 74 | 71 | 81 |
| Hours to 85% Epoxide Selectivity | 80–100 | 80–100 | 20–40 |

I claim:

1. A process for producing propylene oxide comprising
   (a) contacting propylene with an active oxygen species in a liquid phase utilizing a heterogeneous catalyst at a temperature and pressure effective to obtain at least a desired minimum yield of propylene oxide; and
   (b) increasing both the temperature and pressure in a manner effective to maintain a substantially constant concentration of propylene in the liquid phase and to continue to obtain at least the desired minimum yield of propylene oxide.

2. The process of claim 1 wherein the heterogeneous catalyst is a titanium-containing zeolite.

3. The process of claim 1 wherein the heterogeneous catalyst is titania-on-silica.

4. The process of claim 1 wherein the heterogeneous catalyst is deployed in the form of a fixed bed or a plurality of fixed beds within a vaporizing reactor.

5. The process of claim 1 wherein step (b) is continued until a point when the desired minimum yield of propylene oxide can no longer be achieved by further increasing the temperature and pressure, at which time the heterogeneous catalyst is replaced or regenerated.

6. A process for producing propylene oxide comprising
   (a) contacting propylene with hydrogen peroxide in a liquid phase within a vaporizing reactor utilizing a titanium-containing zeolite catalyst at a temperature and pressure effective to obtain at least a desired minimum yield of propylene oxide;
   (b) increasing both the temperature and pressure in a manner effective to maintain a substantially constant concentration of propylene in the liquid phase and to continue to obtain at least the desired minimum yield of propylene oxide; and
   (c) regenerating the titanium-containing zeolite catalyst when the titanium-containing zeolite catalyst performance has declined to a point when the desired minimum yield of propylene oxide can no longer be achieved by further increasing the temperature and pressure.

7. The process of claim 6 wherein the titanium-containing zeolite catalyst is a titanium silicalite.

8. The process of claim 6 wherein the desired minimum yield of propylene oxide is 80%.

9. The process of claim 6 wherein the temperature during steps (a) and (b) is maintained in the range of from 40° C. to 80° C.

10. The process of claim 6 wherein the pressure during steps (a) and (b) is maintained in the range of from 150 to 1000 psia.

11. The process of claim 6 wherein the propylene concentration in the liquid phase during steps (a) and (b) is from 20 to 60 weight percent.

12. The process of claim 6 wherein the liquid phase is additionally comprised of a $C_1$–$C_6$ aliphatic alcohol.

13. The process of claim 6 wherein step (c) is accomplished by washing the titanium-containing zeolite catalyst with a solvent.

14. The process of claim 13 wherein the solvent is selected from the group consisting of $C_1$–$C_6$ aliphatic alcohols, water and mixtures thereof.

15. The process of claim 13 wherein the solvent contains a source of a cation selected from the group consisting of ammonium, alkali metal cations, and mixtures thereof.

16. The process of claim 13 wherein said washing is performed at a temperature of from 150° C. to 250° C.

* * * * *